(12) United States Patent
Nishimura et al.

(10) Patent No.: US 10,573,405 B2
(45) Date of Patent: Feb. 25, 2020

(54) GENOME ANALYSIS AND VISUALIZATION USING COVERAGES FOR BIN SIZES AND RANGES OF GENOMIC BASE COORDINATES CALCULATED AND STORED BEFORE AN OUTPUT REQUEST

(71) Applicant: XCOO INC., Tokyo (JP)

(72) Inventors: Kunihiro Nishimura, Tokyo (JP); Takashi Aoki, Tokyo (JP); Satomi Sakata, Tokyo (JP); Toshiki Takeuchi, Tokyo (JP); Yuki Ban, Tokyo (JP); Atsuo Yamada, Tokyo (JP); Satoshi Kondo, Tokyo (JP)

(73) Assignee: XCOO INC., Tokyo (JP)

( * ) Notice: Subject to any disclaimer, the term of this patent is extended or adjusted under 35 U.S.C. 154(b) by 120 days.

(21) Appl. No.: 15/532,810

(22) PCT Filed: Apr. 28, 2016

(86) PCT No.: PCT/JP2016/063509
§ 371 (c)(1),
(2) Date: Jun. 2, 2017

(87) PCT Pub. No.: WO2016/175330
PCT Pub. Date: Nov. 3, 2016

(65) Prior Publication Data
US 2017/0372003 A1    Dec. 28, 2017

(30) Foreign Application Priority Data

Apr. 30, 2015 (JP) ................. 2015-093739

(51) Int. Cl.
*G16B 30/00* (2019.01)
*G16B 20/00* (2019.01)
*G16B 45/00* (2019.01)
*G16B 50/00* (2019.01)

(52) U.S. Cl.
CPC ............ *G16B 30/00* (2019.02); *G16B 20/00* (2019.02); *G16B 45/00* (2019.02); *G16B 50/00* (2019.02)

(58) Field of Classification Search
None
See application file for complete search history.

(56) References Cited

FOREIGN PATENT DOCUMENTS

| JP | H08110909 A | 4/1996 |
|---|---|---|
| JP | 2002091991 A | 3/2002 |
| JP | 2005234697 A | 9/2005 |
| JP | 2011229817 A | 11/2011 |
| JP | 2013126131 A | 6/2013 |
| JP | 2014505935 A | 3/2014 |
| KR | 10-2014-0135945 A | 11/2014 |
| WO | 2013024810 A1 | 2/2013 |
| WO | 2013/086355 A1 | 6/2013 |

OTHER PUBLICATIONS

International Search Report dated May 31, 2016 for PCT/JP2016/063509 and English translation.
Jin Hong, et al., "GVis: A Scalable Visualization Framework for Genomic Data," Joint Eurographics/IEEE VGTC Symposium on Visualization, 2005 (9 pages).
Ozer Hatice Gulcin, et al., "A Comprehensive Analysis Workflow for Genome-wide Screening Data from ChIP-Sequencing Experiments," International Conference on Simulation, Modeling, and Programming for Autonomous Robots 2010, Springer, Berlin, Heidelberg, pp. 320-330.
Pinard Robert, et al., "Assessment of Whole Genome Amplification-Induced Bias through High-Throughput, Massively Parallel Whole Genome Sequencing," BMC Genomics, Biomed Central, vol. 7, No. 1, Aug. 23, 2006, pp. 216-237.
EPO, Extended European Search Report for corresponding European Patent Application No. 16786606.0, dated Nov. 28, 2018 (10 pages).
KIPO, Notification of Reasons for Refusal for corresponding Korean Patent Application No. 10-2017-7017545, dated Dec. 11, 2018, with machine English Translation (8 pages).
KIPO, Office Action for the corresponding Korean patent application No. 10-2017-7017545, dated Sep. 23, 2019, with English translation (7 pages).
Magnus Nåslund, "Web-based Mapping: An Evaluation of Four JavaScript APIs," Final Thesis in Computer and Information Science at Linkoping Institute of Technology, 2007, Linköping, Sweden.

*Primary Examiner* — G Steven Vanni
(74) *Attorney, Agent, or Firm* — Lucas & Mercanti, LLP

(57) ABSTRACT

There is provided a genome analysis device configured to analyze genome data including a large quantity of fragmented genome base sequences, and transmit output data concerning the genome data in response to an output request from a client device connected via a network, the genome analysis device including; a storage unit for storing data for visualization of multiple different layers, for the genome data; a request receiving unit for receiving an output request from the client device; and an output data generating unit for selecting data for visualization of a layer corresponding to the output request from the storage when the request receiving unit receives the output request, and generating output data based on the data for visualization of the selected layer.

7 Claims, 17 Drawing Sheets
Specification includes a Sequence Listing.

[FIG1]
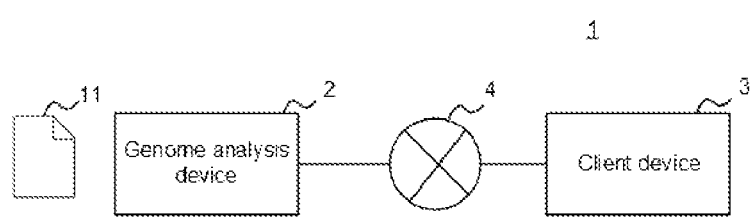

[FIG2]
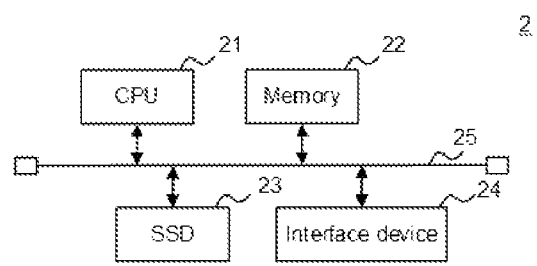

[FIG3]
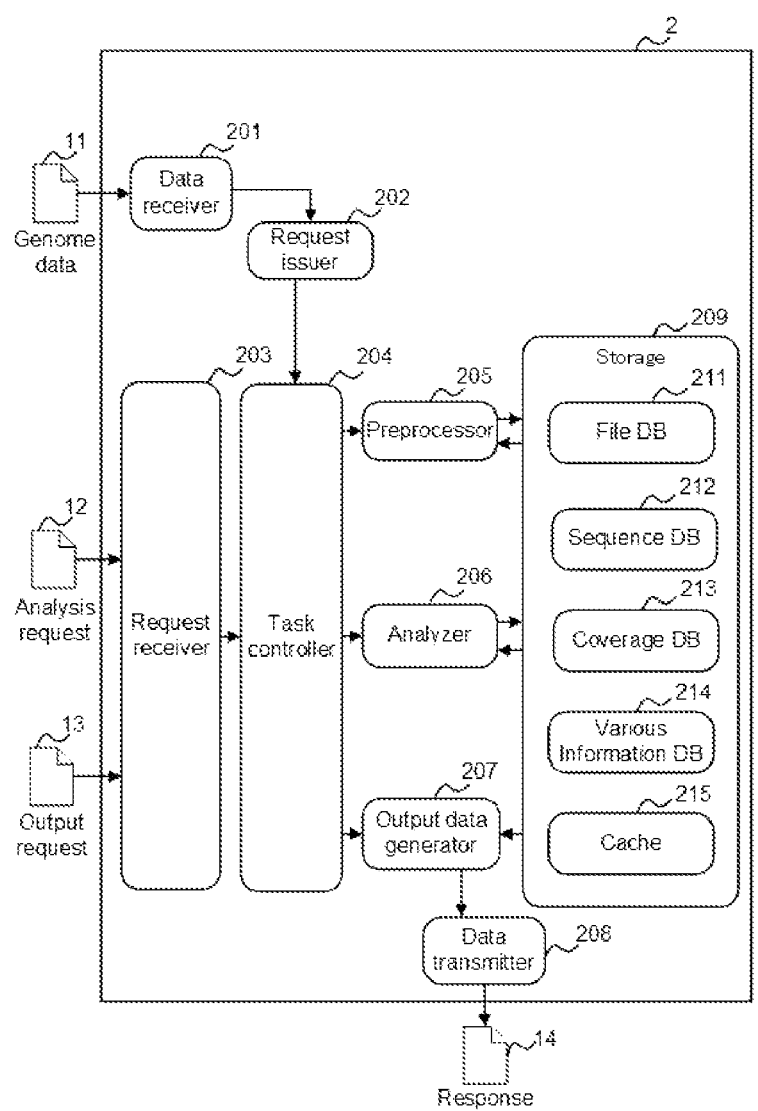

[FIG4]
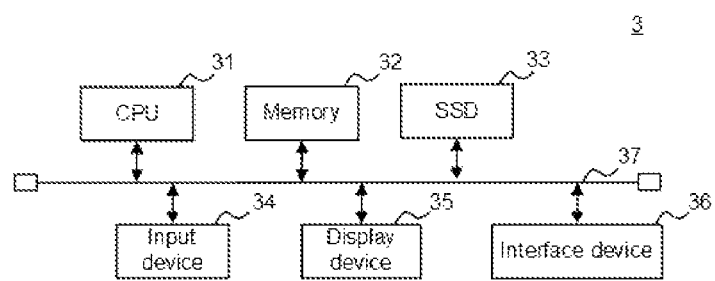

[FIG5]
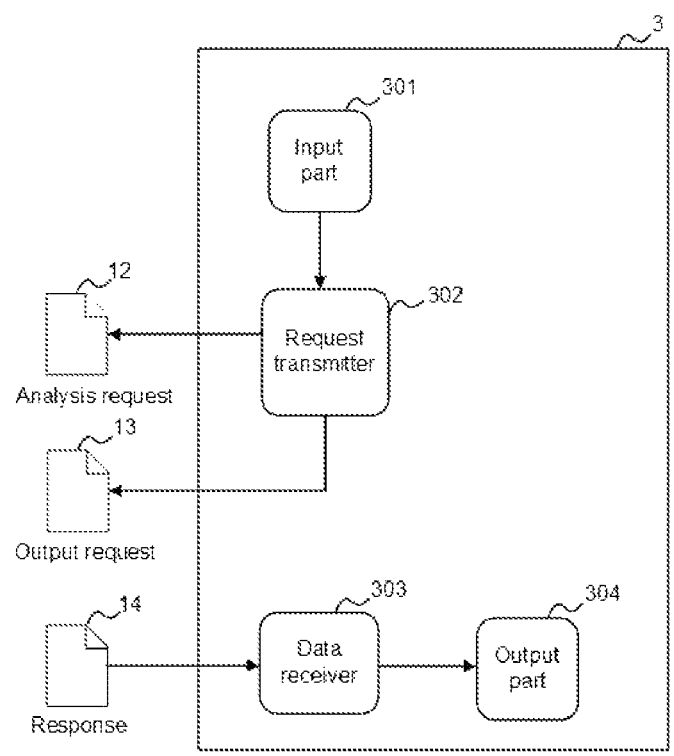

[FIG6]
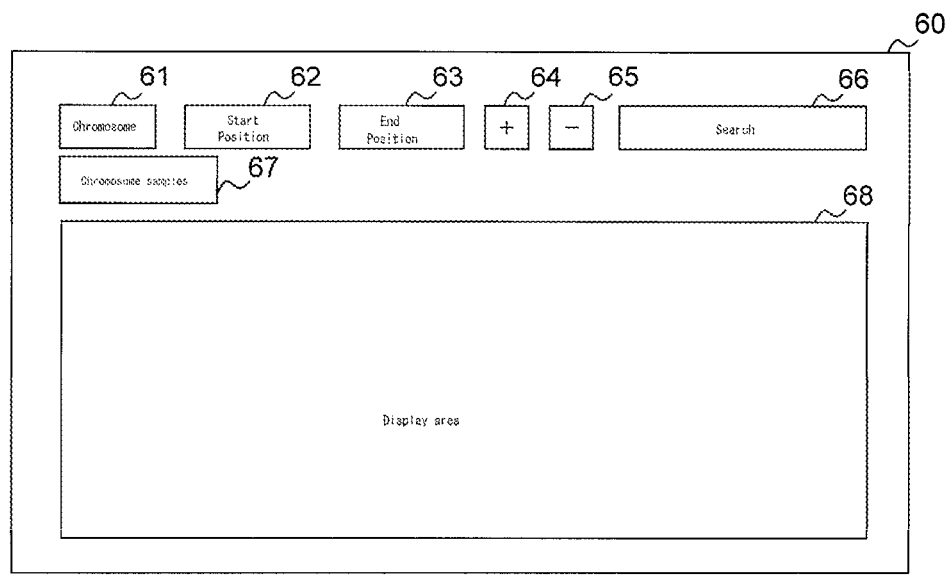

[FIG7]
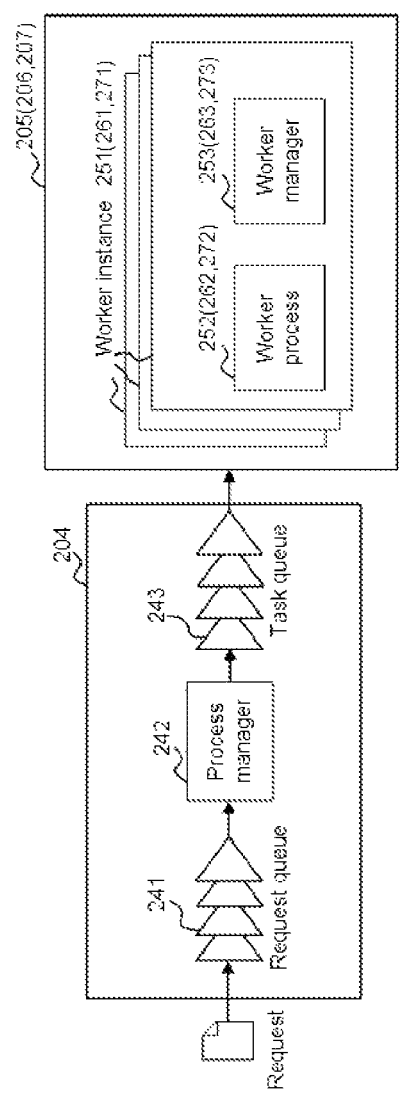

[FIG8]
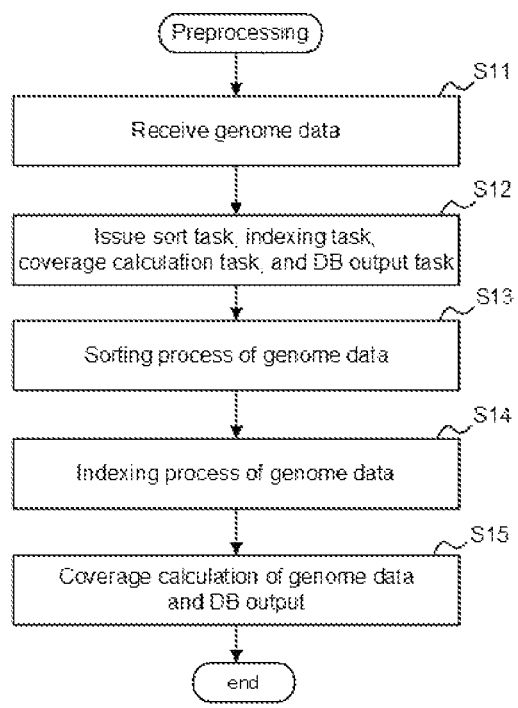

[FIG9]
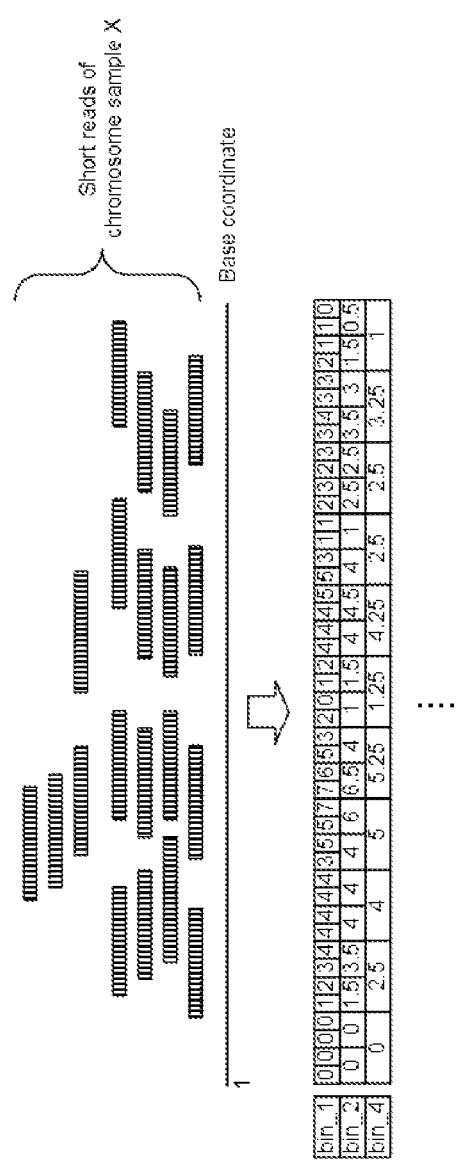

[FIG10]

| Bin size | Base coordinate | Coverage | Base coordinate | Coverage | Base coordinate | Coverage | Base coordinate | Coverage |
|---|---|---|---|---|---|---|---|---|
| 512 | (1, 512) | ×× | (513, 1024) | ××× | (1025, 1536) | ×××× | | |
| 1024 | (1, 1024) | △△ | (1025, 2048) | △△△ | (2049, 3072) | △△△△ | | |
| 2048 | (1, 2048) | ●● | (2049, 4096) | ●●● | (4097, 6144) | ●●●● | | |
| ⋮ | ⋮ | ⋮ | ⋮ | ⋮ | ⋮ | ⋮ | ⋮ | ⋮ |

101   102A  102B  103A  103B  104A  104B   100

[FIG11]
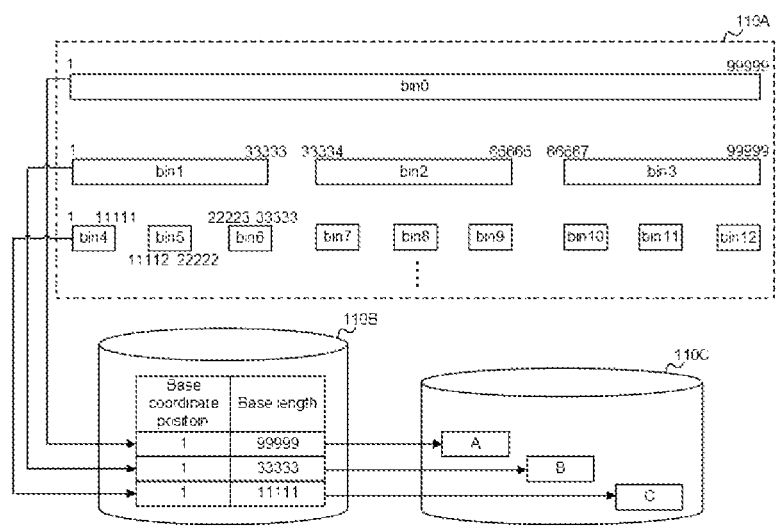

[FIG12]
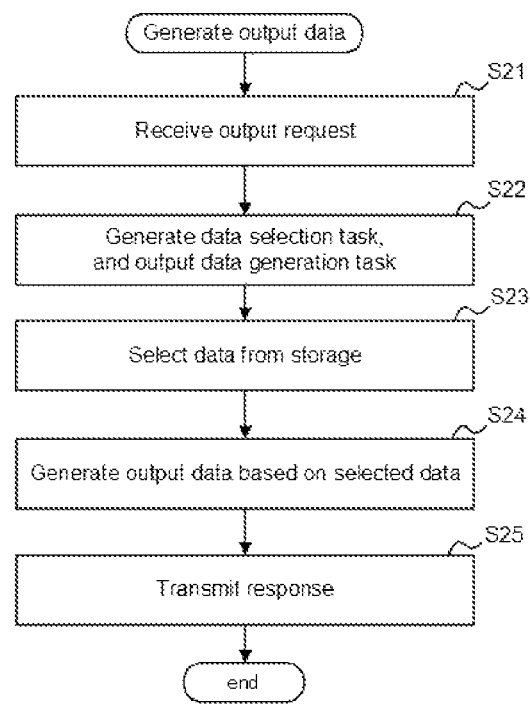

[FIG13]
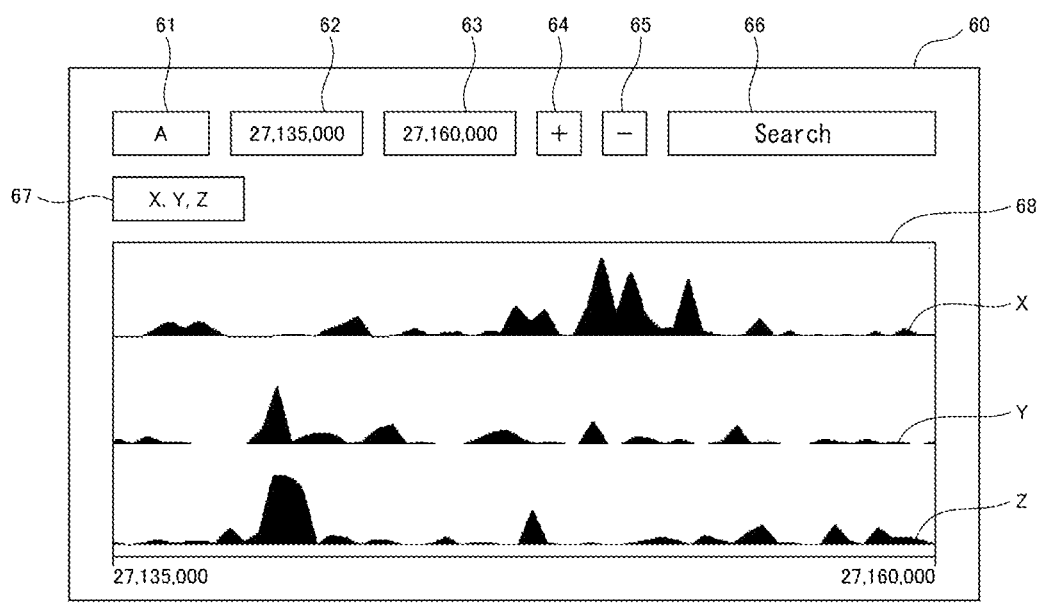
[FIG14]
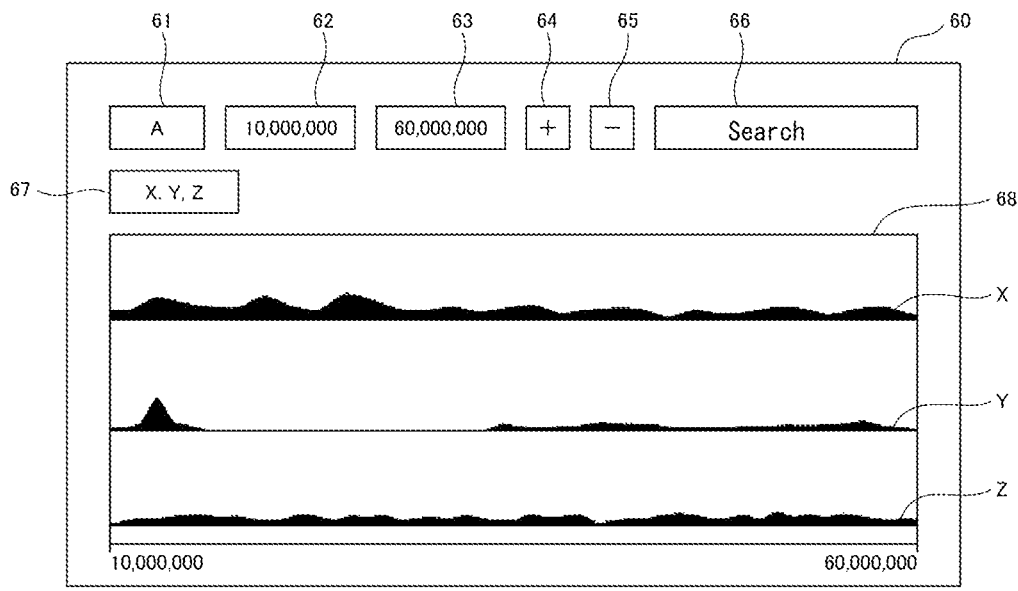

[FIG15]
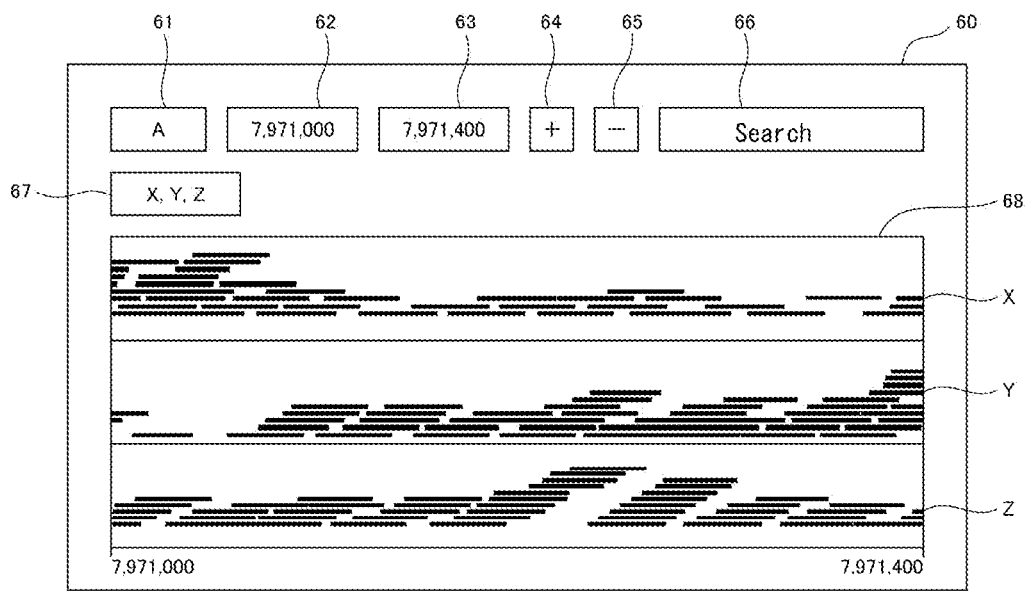
[FIG16]
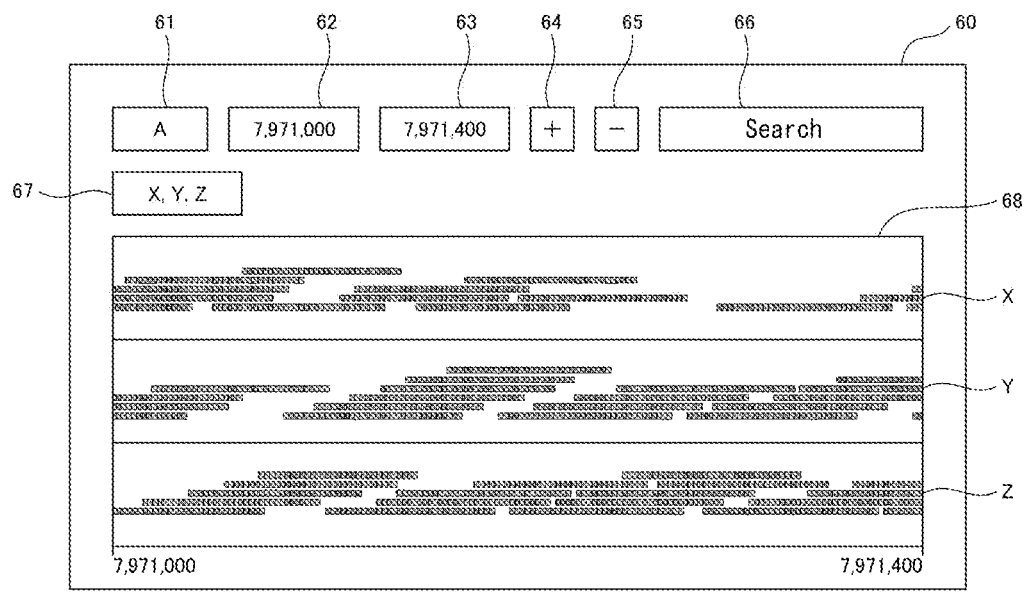

[FIG17]
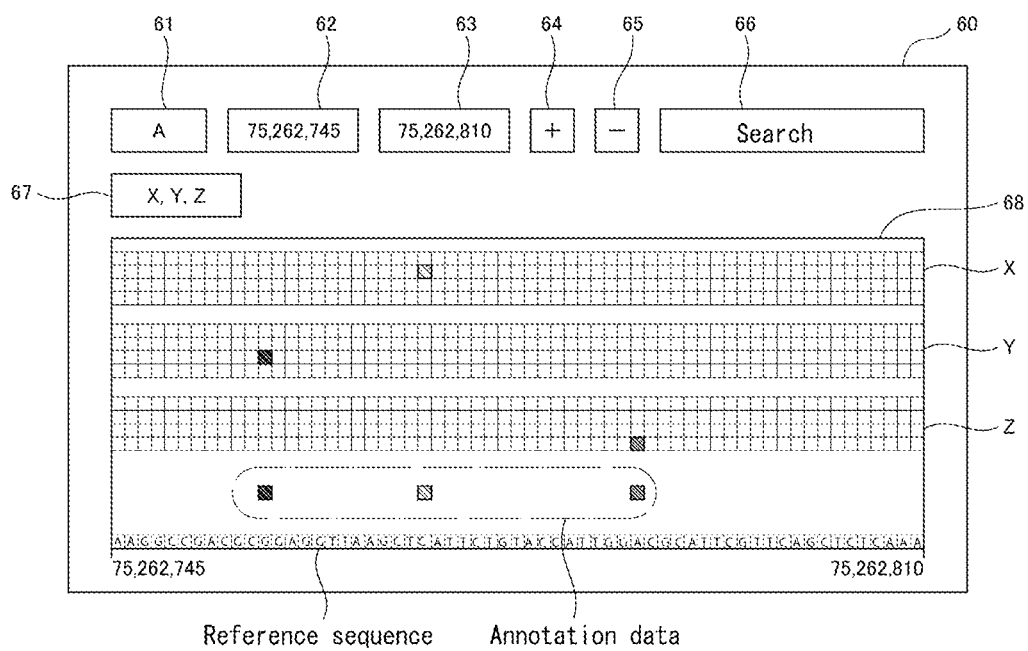

[FIG18]

| Gene name | Chromosome locus | Exon | Mutation | dbSNP | Mutation frequency of target gene in target disease | Mutation frequency in target gene in mutated target disease |
|---|---|---|---|---|---|---|
| KRAS | 12p12.1 | exon 2 | c.35G>A(G12D) | rs112445441 | 36-40% (Amado et al. 2008; Faulkner et al. 2010; Neumann et al. 2009) | 33.5-34.4% (Faulkner et al. 2010) |
| KRAS | 12p12.1 | exon 2 | c.37G>T(G13C) | rs121913535 | 36-40% (Amado et al. 2008; Faulkner et al. 2010; Neumann et al. 2009) | <1% (Faulkner et al. 2010) |

Drug response: There is a high possibility that a patient with RAS gene (KRAS/NRAS gene) cannot obtain benefits (life-prolonging effect, tumor shrinkage) by administration with an anti-EGFR antibody drug

| Drug name | Effect |
|---|---|
| cetuximab | × |
| panitumumab | × |

Source: [Guidance regarding measurement of RAS gene (KRAS/NRAS gene) mutation in patients with colon cancer, XX Academic Society]

[FIG19]

| Gene name | Chromosome locus | Exon | Mutation | dbSNP | Mutation frequency of target gene in target disease | Mutation frequency in target gene in mutated target disease |
|---|---|---|---|---|---|---|
| PIK3CA | 3q26.3 | exon 9 | c.1624G>A(E542K) | rs121913273 | 26% (Saal et al. 2005; Stemke-Hale et al. 2008; O'Brien et al. 2010) | ~11% |
| PIK3CA | 3q26.3 | exon 9 | c.1633G>A(E545K) | rs104886003 | 26% (Saal et al. 2005; Stemke-Hale et al. 2008; O'Brien et al. 2010) | ~20% |
| PIK3CA | 3q26.3 | exon 9 | c.3140A>G(H1047R) | rs121913279 | 26% (Saal et al. 2005; Stemke-Hale et al. 2008; O'Brien et al. 2010) | ~55% |

| Drug response | According to the result of biomarker analysis in CHER-LOB clinical study (phase II study), co-administration of Trastuzumab and Lapatinib is less effective than single administration of these in PIK3CA mutation positive, HER2-positive breast cancer patients |
|---|---|

| Drug name | Effect |
|---|---|
| Trastuzumab + Lapatinib | × |

| Source | http://www.aaa.com:bbb/ccc/ddd |
|---|---|

GENOME ANALYSIS AND VISUALIZATION USING COVERAGES FOR BIN SIZES AND RANGES OF GENOMIC BASE COORDINATES CALCULATED AND STORED BEFORE AN OUTPUT REQUEST

CROSS REFERENCE TO RELATED APPLICATION

This application is a 371 of PCT/JP2016/063509 filed on Apr. 28, 2016, which, in turn, claimed the priority of Japanese Patent Application No. 2015-093739 filed on Apr. 30, 2015, both applications are incorporated herein by reference.

TECHNICAL FIELD

The present invention relates to a genome analysis device and a genome visualization method.

BACKGROUND ART

In the 1990s, genome projects were launched for the purpose of understanding the principles of organisms, further studying diseases of organisms, and studying the origins and evolution by analyzing the whole genetic information included in DNA and RNA possessed by an organism, namely, the whole genomic base sequence.

A genomic base sequence to be analyzed contains vast quantities of data per one sample. In recent years, a sequence decoding device, which is called a next generation sequencer, capable of decoding a genomic base sequence at very high speed and at low cost has been developed and brought into practice.

The next generation sequencer reads DNA or RNA at high speed by fragmenting DNA or RNA to be analyzed into very short fragments (named, short reads) and reading these fragments in parallel, and analyzes each of the read fragments to determine a base sequence of each fragment. Thereafter, the determined base sequence information of each fragment is output as sequence data called a read sequence, for example, data in the FASTQ format. Alternatively, data obtained by aligning (mapping) the read sequence to a known genomic base sequence (hereinafter, also referred to as "reference sequence"), for example, data in the SAM format or the BAM format is output (see Patent Literature 1, for example).

Patent Literature 1 discloses the technique of enabling high quality alignment by the step of specifying a plurality of high quality read sequences from a plurality of read sequences, the step of extracting a plurality of unique read sequences from the plurality of high quality read sequences, and the step of comparing the plurality of unique read sequences with a reference sequence corresponding to a reference sample.

The data in the FASTQ format, SAM format, BAM format, or the like of a chromosome sample (hereinafter, also referred to as "genome data" as a general term) output by the next generation sequencer is utilized for various analyses including ChIP-Seq (Chromatin Immunoprecipitation-sequence) and RNA-Seq.

Meanwhile, a visualization technique that enables analytical results of ChIP-Seq, RNA-Seq, and the like, and genomic base sequences to be visually grasped is also developed. Examples of the visualization technique include viewers such as Integrative Genomics Viewer (Broad Institute in the U.S.), Integrated Genome Browser (Affymetrix in the U.S.), UCSC Genome Browser (University of California, Santa Cruz in the U.S.), Gbrowse and the like can be recited.

According to these visualization techniques, it is possible to visually compare the commonness, difference, or the like between the reference sequence and the genomic base sequence that is reconstructed by assembling a large number of read sequences.

CITATION LIST

Patent Literature

Patent Literature 1: JP 2014-505935 A

SUMMARY OF THE INVENTION

Technical Problems

In Web browser type viewers like the UCSC Genome Browser, and the Gbrowse, when a user intends to change the display range after once displaying a genomic base sequence in a predetermined display range, a lot of time is required for updating the display range, and thus it has been impossible to conduct seamless visualization on the Web browser. To be more specific, when a user inputs a display range change instruction on the Web browser, a Web server or an API server receiving the input display range change instruction from the Web browser is required to recalculate display data based on a large number of read sequences depending on the instruction, and transmit the recalculated display data to the Web browser. Therefore, a lot of time is required every time the display range is changed, and it has been impossible to conduct seamless visualization on the Web browser.

On the other hand, in a standalone viewer like the Integrative Genomics Viewer, and the Integrated Genome Browser, although a certain degree of seamless visualization can be conducted, high specifications are required for the computer device itself into which such a viewer is installed, or special software is required to be additionally installed.

The present invention has been devised in light of the circumstances as described above, and it is an object of the present invention to provide a genome analysis device and a genome visualization method easily enabling seamless visualization by using the mechanism of the Web browser.

Solution to Problems

In order to achieve the above object, a genome analysis device according to the present invention is a genome analysis device configured to analyze genome data including a large quantity of fragmented genome base sequences, and transmit output data concerning the genome data in response to an output request from a client device connected via a network, the genome analysis device including; a storage unit for storing data for visualization of multiple different layers, for the genome data; a request receiving unit for receiving an output request from the client device; and an output data generating unit for selecting data for visualization of a layer corresponding to the output request from the storage when the request receiving unit receives the output request, and generating output data based on the data for visualization of the selected layer.

Also, in order to achieve the above object, a genome visualization method in a genome analysis device that includes a storage unit for storing data concerning genome data including a large quantity of fragmented genome base sequences, the genome analysis device configured to analyze the genome data and transmit output data concerning the genome data in response to an output request from a client device connected via a network, the storage unit storing data for visualization of multiple different layers for the genome data, the genome visualization method including; a request receiving step of receiving an output request from the client device; and an output data generating step of selecting data for visualization of a layer corresponding to the output request from the storage when the output request is received in the request receiving step, and generating output data based on the data for visualization of the selected layer.

Advantageous Effects of Invention

According to the present invention, it is possible to easily enable seamless visualization by using the mechanism of the Web browser.

BRIEF DESCRIPTION OF THE DRAWINGS

FIG. 1 is a diagram showing a system configuration example of a genome analysis system according to the present embodiment.

FIG. 2 is a diagram showing a hardware configuration example of the genome analysis device according to the present embodiment.

FIG. 3 is a diagram showing a functional configuration example of the genome analysis device according to the present embodiment.

FIG. 4 is a diagram showing a hardware configuration example of a client device according to the present embodiment.

FIG. 5 is a diagram showing a functional configuration example of the client device according to the present embodiment.

FIG. 6 shows one example of a screen displayed in the client device according to the present embodiment.

FIG. 7 is a diagram for illustrating a task controller, a preprocessor, an analyzer, and an output data generator of the genome analysis device according to the present embodiment.

FIG. 8 is a flowchart showing one example of a control logic concerning preprocessing of the genome analysis device according to the present embodiment.

FIG. 9 is a chart for illustrating one example of the processing in step S15 of FIG. 8.

FIG. 10 is a chart showing one example of a coverage DB of the genome analysis device according to the present embodiment.

FIG. 11 is a chart for illustrating one example of various information DB of the genome analysis device according to the present embodiment.

FIG. 12 is a flowchart showing one example of a control logic concerning output data generation of the genome analysis device according to the present embodiment.

FIG. 13 shows a first specific example of a display screen provided by the genome analysis device according to the present embodiment.

FIG. 14 shows a second specific example of a display screen provided by the genome analysis device according to the present embodiment.

FIG. 15 shows a third specific example of a display screen provided by the genome analysis device according to the present embodiment.

FIG. 16 shows a fourth specific example of a display screen provided by the genome analysis device according to the present embodiment.

FIG. 17 shows a fifth specific example of a display screen provided by the genome analysis device according to the present embodiment. This figure shows SEQ ID No. 1: AAGGCCGACGCGGAGGTTAAGCTCATTCTGTAC-CATTGGACGCATTCGTTCAGCTCTCAAA.

FIG. 18 shows a first specific example of report data output by the genome analysis device according to the present embodiment.

FIG. 19 shows a second specific example of report data output by the genome analysis device according to the present embodiment.

DESCRIPTION OF EMBODIMENT

Hereinafter, an embodiment of the present invention will be described.

FIG. 1 is a diagram showing a system configuration example of a genome analysis system of the present embodiment. A genome analysis system 1 shown in FIG. 1 includes a genome analysis device 2 and a client device 3 connected via a network 4 such as the Internet.

Genome data 11 is large-quantity fragmented base sequence information output from a next generation sequencer, for example, sequence data that is called read sequences in the FASTQ format, or data obtained by mapping the read sequences on a reference sequence, for example, data in the SAM format, or the BAM format. The genome data 11 is input to the genome analysis device 2.

The genome analysis device 2 is a device to which the genome data 11 is input, and conducts various analyses such as ChIP-Seq, RNA-Seq, and mutation analysis for the input genome data 11. The genome analysis device 2 functions as an application server that conducts, in response to an analysis request from the client device 3 connected via the network 4, analysis according to the analysis request.

The genome analysis device 2 generates output data concerning the genome data 11 in response to an output request from the client device 3, and transmits the output data to the client device 3. The output data as used herein refers to Web page data (hereinafter, also referred to as "display data"), or report data representing an analysis result or the like in the table format, the PDF format, or the like. In particular, when the output data is display data, the genome analysis device 2 functions as a Web server.

The client device 3 transmits an analysis request that is input by a user on the device to the genome analysis device 2. The client device 3 transmits an output request to the genome analysis device 2. The output request as used herein refers to a request concerning display of the aforementioned display data (hereinafter, also referred to as "display request") or a request concerning output of the aforementioned report data. In particular, when the output request is a display request, the client device 3 functions as a Web client, and has a Web browser type viewer that displays the display data received from the genome analysis device 2.

With the foregoing configuration, in the genome analysis system 1 according to the present embodiment, the genome analysis device 2 analyzes the genome data 11, and transmits output data representing an analysis result or the like to the client device 3. The genome analysis device 2 may be a group of servers constructed on the cloud or may be an on-premises server.

FIG. 2 is a diagram showing a hardware configuration example of the genome analysis device 2 according to the present embodiment. In the following description, the same constituent as that described before is denoted by the same reference numeral, and the overlapping description will be omitted as appropriate.

The genome analysis device 2 shown in FIG. 2 includes a CPU (Central Processing Unit) 21, memory 22, an SSD (Solid State Drive) 23, and an interface device 24, which are connected via a bus 25. The CPU 21 is a central processing unit for executing various programs stored in the memory 22. The memory 22 is a storage device such as RAM (Random Access Memory) for storing a program executed by the CPU 21, and data used by the program. The SSD 23 is a storage device for storing various data and the like. The SSD 23 may be an HDD (Hard Disk Drive). The interface device 24 is an interface device for connecting to the network 4 (see FIG. 1) or the like.

The genome analysis device 2 is not limited to the case where it is physically a single computer. The genome analysis device 2 may be configured by a combination of a plurality of computers, or may be a virtual server provided virtually on the cloud by using a virtualization technique.

FIG. 3 is a diagram showing a functional configuration example of the genome analysis device 2 according to the present embodiment.

The genome analysis device 2 shown in FIG. 3 has a data receiver 201, a request issuer 202, a request receiver 203, a task controller 204, a preprocessor 205, an analyzer 206, an output data generator 207, a data transmitter 208, and a storage 209.

The data receiver 201 receives the genome data 11 of a predetermined chromosome sample including a large quantity of fragmented genome base sequences. The reception may be conducted by manual or automatic uploading from the computer device (not shown in FIG. 1) that is connected via the network 4 and stores the genome data 11, or may be conducted by importing the genome data 11 on the cloud.

When the data receiver 201 receives the genome data 11, the request issuer 202 internally issues a request for storing the received genome data 11 in the storage 209.

The request receiver 203 receives an analysis request 12 or an output request 13, which are transmitted from the client device 3. The analysis request 12 is a request concerning analysis such as ChIP-Seq, RNA-Seq, mutation analysis, and analysis concerning a predetermined disease, for example, colon cancer or breast cancer. The output request 13 is a display request or a request concerning output of report data. In the display request, designation of chromosome and base coordinate to be displayed, an instruction of scaling, designation of a chromosome sample to be displayed, an instruction of search, and the like are described. Meanwhile, in the request concerning output of report data, an output data format (table format, PDF format, etc.) and designation of a gene to be output, and the like are described.

When the request issuer 202 issues a request, or the request receiver 203 receives the analysis request 12 or the output request 13, the task controller 204 conducts generation and management of tasks.

In particular, when the request issuer 202 issues a request, the task controller 204 generates a task to be executed by the preprocessor 205. When the request receiver 203 receives the analysis request 12, the task controller 204 generates a task to be executed by the analyzer 206. Further, when the request receiver 203 receives the output request 13, the task controller 204 generates a task to be executed by the output data generator 207.

The preprocessor 205 performs preprocessing for the genome data 11 by parallel distributed processing. The preprocessing as used herein refers to preprocessing of the analysis to be conducted by the analyzer 206. Various data generated as a result of the preprocessing by the preprocessor 205 is stored in the storage 209. When the genome data 11 is sequence data in the FASTQ format, the preprocessor 205 reads in information of a reference sequence stored in a sequence DB 212 of the storage 209, and conducts processing of mapping the sequence data in the FASTQ format on the reference sequence as preprocessing.

The analyzer 206 conducts analysis concerning the analysis request 12 for the data stored in the storage 209 by parallel distributed processing. The analysis result by the analyzer 206 is stored in the storage 209.

The output data generator 207 conducts generation of output data concerning the output request 13 by parallel distributed processing based on the data stored in the storage 209.

The data transmitter 208 transmits the output data generated by the output data generator 207 to the client device 3 as a response 14 for the output request 13.

The storage 209 stores data generated as a result of the preprocessing by the preprocessor 205, an analysis result by the analyzer 206, data concerning annotation and mutation information (hereinafter, also generally called "annotation data") previously acquired from a public database, and the like. The storage 209 includes a file DB 211, the sequence DB 212, a coverage DB 213, a various information DB 214, and a cache 215.

The file DB 211 is a storage unit for storing file information of the input genome data 11 of a predetermined chromosome sample. The file information as used herein refers to information of condition of the chromosome sample, information of chromosome in the chromosome sample, information of tags used for management, bookmark information (chromosome and base coordinate), layout information (data set of the chromosome sample), and the like.

The information of tags is information for facilitating search of the genome data 11. The bookmark information includes a combination of chromosome and base coordinate. By storing the bookmark information, it becomes possible to read in the genome data 11 of a desired chromosome sample at high speed by designation of chromosome and base coordinate. The layout information is a data set of a chromosome sample. By storing the layout information, it becomes possible to read in, at a time, a data set of a chromosome sample desired to be displayed.

The sequence DB 212 is a storage unit for storing information of a reference sequence (known genomic sequence) for each chromosome previously acquired from a public database or the like. Concretely, for each chromosome, base sequence information of ATGC of the reference sequence is stored as a sequential byte sequence described by one byte per one character. This enables high-speed search and random access to arbitrary coordinates by designating the start position and the end position of the base coordinate.

The coverage DB 213 is a storage unit for storing information of coverage between the input genome data 11, and the reference sequence of the chromosome corresponding to the genome data 11. Coverage is provided for overlooking the quantity of data, and is calculated by the preprocessor 205. In the coverage DB 213, coverage is stored by taking the chromosome and the base coordinate as a key. This enables high-speed search and random access to arbitrary coordinates. Detailed description for the coverage DB 213 will be made later with reference to FIG. 9 and FIG. 10.

The various information DB 214 is a storage unit for storing various genomic information including annotation data and mutation information, and alignment of each genome data 11.

The annotation data is data generated from public gene information, such as RefSeq (Reference Sequence) that is previously acquired from a public database or the like. The mutation information is public mutation information, such as dbSNP (Single Nucleotide Polymorphism) that is previously acquired from a public database or the like. The alignment refers to a base coordinate of fragmented data constituting the input genome data 11 (hereinafter, also referred to as "fragmented data"), and the base coordinate is determined by referring to a reference sequence.

As is the case with the coverage DB 213, in the various information DB 214, various information is stored by taking the chromosome and the base coordinate as a key. This enables high-speed searches and random access to arbitrary coordinates. Detailed description for the various information DB 214 will be made later with reference to FIG. 11.

The various information DB 214 also stores new (improved) annotation data or the like that is generated by analysis made by the analyzer 206 using the annotation data stored in the various information DB 214. The various information DB 214 also stores annotation data for the genome data 11 generated by the preprocessing by the preprocessor 205.

The cache 215 is a storage unit for caching data that is required when the analyzer 206 carries out analysis or when the output data generator 207 generates output data. That is, the cache 215 is provided for enabling high-speed access to data.

Among the above constituents, the data receiver 201, the request receiver 203, and the data transmitter 208 are implemented by the CPU 21 and the interface device 24 in FIG. 2. The request issuer 202, the task controller 204, the preprocessor 205, the analyzer 206, and the output data generator 207 are implemented by the CPU 21 in FIG. 2. The storage 209 is implemented by the CPU 21, the memory 22, and the SSD 23 in FIG. 2.

The coverage DB 213 and the various information DB 214 store data for visualization of multiple different layers for the genome data 11 generated by the preprocessing or the like by the preprocessor 205. Then, the output data generator 207 selects data for visualization of the layer corresponding to the output request 13, and generates output data based on the selected layer of data for visualization. This makes it possible to easily conduct seamless visualization by using the mechanism of the Web browser without requiring recalculation of output data or the like.

The output data generator 207 has a so-called lookahead function of generating display data in a data range slightly larger than the data range of the display data currently displayed in a display area 68 (see FIG. 6), in generating display data. This enables seamless visualization according to the change in the display range even when the display range is changed, for example, by dragging a mouse (input device 34 in FIG. 4) in the vertical or horizontal direction on the display area 68.

FIG. 4 is a diagram showing a hardware configuration example of a client device according to the present embodiment.

The client device 3 shown in FIG. 4 includes a CPU 31, memory 32, an SSD 33, an input device 34, a display device 35, and an interface device 36, which are connected via a bus 37. The CPU 31, the memory 32, the SSD 33, and the interface device 36 are the same as the CPU 21, the memory 22, the SSD 23, and the interface device 24 in FIG. 2, and hence the description will be omitted herein. The input device 34 is a device for a user to input various information, for example, a keyboard or a mouse. The display device 35 is for example, a display.

FIG. 5 is a diagram showing a functional configuration example of the client device according to the present embodiment.

The client device 3 shown in FIG. 5 has an input part 301, a request transmitter 302, a data receiver 303, and an output part 304.

The input part 301 inputs input information for the input device 34 (see FIG. 4). The input information as used herein refers to instruction information concerning analyses such as ChIP-Seq, RNA-Seq and mutation analysis, instruction information concerning display such as designation of chromosome and base coordinate to be displayed, an instruction of scaling, designation of a chromosome sample to be displayed, an instruction of search, and the like, or designation information such as output data format of report data desired to be output (table format or PDF format) and gene to be output. The request transmitter 302 issues the analysis request 12 or the output request 13 according to the input information in the input part 301, and transmits the request to the genome analysis device 2. The data receiver 303 receives the response 14 transmitted from the genome analysis device 2. The output part 304 analyzes the response 14 received by the data receiver 303, and displays display data on the screen in the display device 35 (see FIG. 4), or outputs report data.

Among the above constituents, the input part 301 and the output part 304 are implemented by the CPU 31 in FIG. 4. The request transmitter 302 and the data receiver 303 are implemented by the CPU 31 and the interface device 36 in FIG. 4.

FIG. 6 is one example of a screen displayed in the client device according to the present embodiment.

One example of a display screen 60 shown in FIG. 6 includes a chromosome designation field 61 for designating a chromosome to be displayed, an input field 62 for inputting a start position of range of base coordinates to be displayed, an input field 63 for inputting an end position, a scale-up button 64 for inputting a scale-up instruction, a scale-down button 65 for inputting a scale-down instruction, a keyword input field 66 for inputting a search keyword, a chromosome sample designation field 67 for designating a chromosome sample to be displayed, and the display area 68 in which display data is displayed. In the display screen 60 configured in this manner, a user can input various instruction information concerning display. When a mouse (input device 34) is dragged vertically or horizontally on the display area 68, display data depending on the dragging direction is displayed. The scale-up or scale-down can be also made by a scroll button of the mouse (input device 34).

FIG. 7 is a diagram for illustrating a task controller, a preprocessor, an analyzer and an output data generator of the genome analysis device 2 according to the present embodiment. Here, parallel distributed processing conducted by the task controller 204, the preprocessor 205, the analyzer 206, and the output data generator 207 in FIG. 3 will be described.

As shown in FIG. 7, the task controller 204 includes a request queue 241, a process manager 242, and a task queue 243.

The request queue 241 is a FIFO type queue that stores requests issued by the request issuer 202 and requests such as the analysis request 12 and the output request 13 (see FIG. 3).

The process manager 242 fetches a request stored in the request queue 241, and generates one or more tasks based on the request. The generated tasks include a parallel task that is executed without waiting for execution end of the previous task, and a sequential task that is executed after end of execution of the previous task. The generated task is stored in the task queue 243 which is a FIFO type queue in principle.

The preprocessor 205 includes one or more worker instances 251. Each worker instance 251 includes a worker process 252 for sequentially fetching executable tasks from the tasks stored in the task queue 243 and actually executing the tasks, and a worker manager 253 for monitoring the operation of the worker process 252.

The number of the worker instances 251 increases or decreases dynamically depending on the number of tasks stored in the task queue 243 and the like, and tasks stored in the task queue 243 are processed by parallel distributed processing. The same is applied to a worker instance 261, a worker process 262, and a worker manager 263 of the analyzer 206, and a worker instance 271, a worker process 272, and a worker manager 273 of the output data generator 207.

As described above, the task controller 204 conducts generation and management of tasks based on a request, and the preprocessor 205, the analyzer 206, and the output data generator 207 conduct parallel distributed processing on the generated tasks. This enables high-speed processing.

The requests stored in the request queue 241 are independent of each other, and a plurality of requests are processed in parallel. The worker instances 251 are independent of each other, and have such a simple mechanism that processes only the object that can be processed by its own instance, and thus easy scale-out is enabled. Further, the request queue 241 and the task queue 243 are not limited to a FIFO type queue. The request queue 241 and the task queue 243 may be other type of queue.

FIG. 8 is a flowchart showing one example of a control logic concerning preprocessing of the genome analysis device 2 according to the present embodiment. Hereinafter, one example of preprocessing when the genome analysis device 2 receives the genome data 11 in the SAM format or the BAM format will be described with reference to FIG. 3 and FIG. 7 as appropriate.

In step S11, the data receiver 201 receives the genome data 11 in the SAM format or the BAM format (S11). Then, the request issuer 202 internally issues a request for storing the received genome data 11 in the storage 209.

Then, the flow proceeds to step S12 where the task controller 204 (process manager 242) generates four tasks: a sort task, an indexing task, a coverage calculation task, and a DB output task of the genome data 11, based on the request (S12). The generated tasks are stored in the task queue 243.

Here, the sort task is a task for rearranging the individual fragmented data of the input genome data 11 into the order of the base sequence. The indexing task is a task for assigning an index to each fragment data rearranged by the sort task. These sort task and indexing task are tasks for speeding up the processing. The coverage calculation task is a task for calculating coverage between the reference sequence (known genomic sequence) and the genome data 11. The DB output task is a task for outputting the calculated coverage to the storage 209 (coverage DB 213).

The flow proceeds to step S13 where the preprocessor 205 (plurality of the worker instances 251) executes a sorting process of the genome data 11 (S13), and subsequently the flow proceeds to step S14 where the preprocessor 205 executes an indexing process (S14).

Then, the flow proceeds to step S15 where the preprocessor 205 (plurality of the worker instances 251) executes coverage calculation of the genome data 11 and output to the storage 209 in parallel (S15). With the processing indicated above, the genome analysis device 2 calculates coverage of the input genome data 11 in the SAM format or the BAM format and outputs the coverage to the coverage DB 213.

FIG. 9 is a chart for illustrating one example of the processing in step S15 of FIG. 8. In the upper part of FIG. 9, a base coordinate, and individual short reads (fragmented data) of chromosome sample X which are the genome data 11 mapped on the reference sequence of a predetermined chromosome are illustrated in a simplified manner. In the example shown in FIG. 9, the leftmost base coordinate is regarded as 1 for convenience of description.

In step S15, the preprocessor 205 calculates coverage in the bin size of 1 (bin_1). The bin size refers to the unit number of bases for which calculation of coverage is to be made. That is, coverage of each base is calculated in this case. In the example shown in FIG. 9, coverage of each base is calculated sequentially from the first base in the manner of 0, 0, 0, 0, 1, 2, 3, 4, 4, . . . .

Next, the preprocessor 205 doubles the bin size, and calculates coverage in the bin size of 2 (bin_2), namely, coverage per two bases. When the bin size is doubled, it is preferred to conduct a correction for eliminating a gap in numerical value of coverage between cases of different bin sizes, for example, by making coverage ½, or calculating a coverage mean value. In the following description, a correction of calculating a mean value of coverage is conducted (hereinafter, the same applies). In the example shown in FIG. 9, coverage per two bases is calculated sequentially from the first base in the manner of 0, 0, 1.5, 3.5, 4, . . . .

Subsequently, the preprocessor 205 further doubles the bin size, and calculates coverage in the bin size of 4 (bin_4), namely, coverage per four bases. In the example shown in FIG. 9, coverage per four bases is calculated sequentially from the first base in the manner of 0, 2.5, 4, 5, 5.25, . . . . Then the preprocessor 205 calculates coverages while repeatedly doubling the bin size. The coverages calculated in this manner are output to the coverage DB 213.

FIG. 10 is a chart showing one example of a coverage DB of the genome analysis device according to the present embodiment. In FIG. 10, one example of the coverage DB 213 is shown by a table 100 (hereinafter, also referred to as "coverage table 100").

Attributes of the coverage table 100 include a bin size 101, a base coordinate 102A, coverage 102B, a base coordinate 103A, coverage 103B, a base coordinate 104A, coverage 104B, and so on.

The bin size 101 is the unit number of bases for which calculation of coverage is to be made. In FIG. 10, the minimum value of the bin size 101 is set at 512 for convenience of description. The base coordinate 102A indicates the base coordinate of the object for calculation of coverage shown by the coverage 102B by combination of the start position and the end position. The coverage 102B is calculated coverage. The same applies also to the base coordinate 103A, the coverage 103B, the base coordinate 104A, the coverage 104B, and so on.

The example shown in FIG. 10 indicates that the coverage of bases of the coordinates 1-512 in the bin size of 512 is "xx", and the coverage of bases of the coordinates 4097-6144 in the bin size of 2048 is " . . . ".

In this manner, in the coverage table 100, the coverage and the base coordinate are stored in correspondence with each other for each of different bin sizes. The coverage table 100 as described above is generated for each chromosome, or for each chromosome sample (input genome data 11). The coverage for each bin size on each line stored in the coverage table 100 is one example of the aforementioned "data for visualization of multiple different layers for the genome data 11".

Thus, when a chromosome, a chromosome sample, or a range of base coordinates that are desired to be displayed are designated by user input on the display screen 60 shown in FIG. 6, the output data generator 207 (see FIG. 3) selects and reads in coverage of the bin size corresponding to the designated chromosome, chromosome sample, and range of base coordinates from the coverage table 100. The output data generator 207 generates display data for displaying a histogram based on the coverage of the selected bin size. As described above, when the output data generator 207 generates display data, the output data generator 207 generates display data of the data range that is slightly broader than the display data of the data range currently displayed in the display area 68 (see FIG. 6). This enables seamless visualization corresponding to the change in the display range even when the display range is changed, for example, by dragging a mouse (input device 34 in FIG. 4) in the vertical or horizontal direction on the display area 68.

For example, when scale-up designation (or scale-down designation) is input on the display screen 60 shown in FIG. 6, the output data generator 207 reads in coverage having the next-smaller bin size (or having the next-larger bin size) from the coverage table 100, and generates display data for displaying a histogram based on the coverage. Thus, even when the range of base coordinates to be displayed is changed, it is possible to easily switch the coverage to be displayed without necessity of recalculating the display data. Therefore, it is possible to easily conduct seamless visualization.

In the example shown in FIG. 9 and FIG. 10, the processing of calculating coverage is repeated while the bin size is doubled, however, the present invention is not limited thereto. For example, the bin size may be tripled or more. Also, the preprocessor 205 may generate data for visualization of multiple different layers according to an index other than the bin size.

FIG. 11 is a chart for illustrating one example of various information DB of the genome analysis device according to the present embodiment.

With reference to FIG. 11, as one example, a data structure of annotation data which is one of the data stored in the various information DB 214 will be described. In the example shown in FIG. 11, the data structure is simply illustrated by assuming the entire base coordinates of the reference sequence as 1 to 99999 for convenience of description.

Annotation data which is public gene information such as, for example, RefSeq previously acquired from a public database or the like is stored by utilizing an N-branch tree (herein N=3) data structure 110A as shown in FIG. 11.

That is, each node constituting the N-branch tree data structure 110A (bin0, bin1, bin2, . . . ) retains a base coordinate (start position, end position) of the node, and a pointer for an intermediate data structure 110B. The intermediate data structure 110B retains a base coordinate position, a base length, and a pointer for a data body 110C. The data body 110C retains data bodies A, B, C of each annotation data having an arbitrary length and arbitrary format.

In this manner, in the various information DB 214, a base coordinate position, a base length, and annotation data are stored in correspondence with each other for each node. That is, for each range of base coordinates specified by a base coordinate position and a base length from the position, the range of base coordinates and annotation data are stored in correspondence with each other.

When the base length is 1, namely, when the range of base coordinates indicates a specific base, annotation data corresponding to the base is stored in correspondence with each other. Meanwhile, when the base length is 2 or more, namely when the range of base coordinates indicates a specific base group, annotation data corresponding to the base group is stored in correspondence with each other.

These N-branch tree data structure 110A, intermediate data structure 110B and data body 110C are generated for each chromosome, or for each chromosome sample (the genome data 11). Such annotation data for each range of base coordinates is one example of the aforementioned "data for visualization of multiple different layers for the genome data 11".

Thus, when a chromosome, a chromosome sample, or a range of base coordinates that are desired to be displayed are designated by user input on the display screen 60 shown in FIG. 6, the output data generator 207 (see FIG. 3) selects and reads in annotation data of the node corresponding to the designated chromosome, chromosome sample, and range of base coordinates from the various information DB 214. The output data generator 207 generates display data for displaying the annotation data of the selected node. As described above, when the output data generator 207 generates display data, the output data generator 207 generates display data of the data range that is slightly broader than the display data of the data range currently displayed in the display area 68 (see FIG. 6). This enables seamless visualization corresponding to the change in the display range even when the display range is changed, for example, by dragging a mouse (input device 34 in FIG. 4) in the vertical or horizontal direction on the display area 68.

For example, when scale-up designation (or scale-down designation) is input on the display screen 60 shown in FIG. 6, the output data generator 207 reads in annotation data of a child node of the local node (or a parent node of the local node), and generates display data for displaying the annotation data. Thus, even when the range of base coordinates to be displayed is changed, it is possible to easily switch the annotation data to be displayed without necessity of recalculating the display data. Therefore, it becomes possible to conduct seamless visualization.

In the example shown in FIG. 11, while description has been made by taking as an example the case where the N-branch tree data structure 110A has a ternary tree structure, the present invention is not limited thereto. For example, a binary tree structure may be employed. In the various information DB 214, data for visualization of multiple different layers may be stored by a data structure other than the N-branch tree data structure.

As described above, the annotation data retained in the data body 110C is public gene information such as RefSeq or the like that is previously acquired from a public database or the like. Therefore, when the gene information in the public database or the like is updated, only the data body 110C is required to be updated while the N-branch tree data structure 110A and the architecture of the intermediate data structure 110B are left unchanged. Also, new (improved)

annotation data or the like that is generated by analysis made by the analyzer 206 using annotation data stored in the various information DB 214 is stored in the data body 110C. Also, annotation data for the genome data 11 generated by preprocessing by the preprocessor 205 is stored.

The various information DB 214 may store the gene and the annotation data in correspondence with each other for each gene. In this case, annotation data for each gene is one example of the aforementioned "data for visualization of multiple different layers for the genome data 11". The details will be described later with reference to FIG. 18 and FIG. 19.

FIG. 12 is a flowchart showing one example of a control logic concerning output data generation of the genome analysis device 2 according to the present embodiment. Hereinafter, one example of processing when the genome analysis device 2 receives the output request 13 will be described with reference to FIG. 3 and FIG. 7 as appropriate.

In step S21, the request receiver 203 receives the output request 13 (S21). Upon this, the flow proceeds to step S22 where the task controller 204 (process manager 242) generates two tasks: a data selection task and an output data generation task, based on the request (S22). The generated tasks are stored in the task queue 243.

The data selection task is a task for selecting and reading out data from the storage 209 according to the description content of the output request 13. When the output request 13 is a display request, the description content of the output request 13 includes a chromosome and a base coordinate to be displayed, an instruction of scaling, designation of a chromosome sample to be displayed, and an instruction of search. When the output request 13 is a request concerning output of report data, the description content of the output request 13 includes designation of output data format of report data desired to be output (table format or PDF format) and gene to be output, and the like. The output data generation task is a task for generating output data based on the data selected and read out by the data selection task.

The flow proceeds to step S23 where the output data generator 207 (plurality of the worker instances 271) selects and reads out data from the storage 209 (S23). Subsequently, the flow proceeds to step S24 where the output data generator 207 generates output data based on the selected and read out data (S24).

Then, the flow proceeds to step S25 where the data transmitter 208 transmits the output data generated by the output data generator 207 to the client device 3 as the response 14 for the output request 13 (S25). By the processing indicated above, the genome analysis device 2 conducts visualization of genome information by transmitting the output data concerning the genome data 11 in response to the output request 13 from the client device 3.

As described above, according to the genome analysis device 2 according to the present embodiment, upon reception of the output request 13 from the client device 3, the genome analysis device 2 selects data for visualization of the layer corresponding to the output request 13 from the storage 209, and generates output data based on the data for visualization of the selected layer. Therefore, particularly, when the output data is display data, and the display range is desired to be changed after the genome data 11 is once displayed in a predetermined display range, it becomes possible to easily conduct seamless visualization by using the mechanism of the Web browser without necessity of recalculating the display data.

FIG. 13 to FIG. 17 respectively show first to fifth specific examples of a display screen provided by the genome analysis device according to the present embodiment.

In the first specific example shown in FIG. 13, chromosome A is input in the chromosome designation field 61, "27,135,000" is input in the start position input field 62 and "27,160,000" is input in the end position input field 63 of the range of base coordinates to be displayed, and chromosome samples X, Y, Z is input in the chromosome sample designation field 67.

Therefore, in the display area 68, coverage between chromosome samples X, Y, Z and chromosome A in the range of base coordinates between 27,135,000 and 27,160,000 (base number 25,000) is displayed by a histogram. In this manner, many chromosome samples can be compared on one screen.

When the scale-down button 65 is pressed on the display screen 60, the output data generator 207 in FIG. 3 selects coverage (see FIG. 10) having a larger bin size than the coverage used in this screen display, and generates display data based on the coverage of the selected bin size. As a result, the screen is shifted to the screen as shown in FIG. 14.

In the second specific example shown in FIG. 14, "10,000,000" is input in the start position input field 62 and "60,000,000" is input in the end position input field 63 of the range of base coordinates to be displayed. Accordingly, in the display area 68, the range between 10,000,000 and 60,000,000 (base number 50,000,000) is indicated as the range of base coordinates, and thus the display range is larger than the range of base coordinates in FIG. 13.

When the scale-up button 64 is pressed on the display screen 60 shown in FIG. 13, the output data generator 207 in FIG. 3 selects coverage (see FIG. 10) having a smaller bin size than the coverage used in this screen display, and generates display data based on the coverage of the selected bin size. The screen may be shifted to the screen as shown in FIG. 15 and FIG. 16.

In the third specific example shown in FIG. 15 and the fourth specific example shown in FIG. 16, "7,971,000" is input in the start position input field 62 and "7,974,000" is input in the end position input field 63 of the range of base coordinates to be displayed. Accordingly, in the display area 68 of FIG. 15 and FIG. 16, the range between 7,971,000 and 7,974,000 (base number 3,000) is indicated as the range of base coordinates, and thus the display range is smaller than the range of base coordinates in FIG. 13.

In the display area 68 of FIG. 15, a mode in which each fragmented data of chromosome samples X, Y, Z is mapped on the reference sequence (not shown in FIG. 15) is displayed in place of a histogram. When the display is scaled up to a certain degree or more, the output data generator 207 in FIG. 3 may generate display data indicating the mapping mode of each fragmented data.

On the other hand, in the display area 68 of FIG. 16, each base constituting each fragmented data of chromosome samples X, Y, Z is displayed in a distinguishable mode. When the display is scaled up to a certain degree or more in this manner, the output data generator 207 in FIG. 3 may generate display data indicating each base constituting each fragmented data in a distinguishable mode.

In the fifth specific example shown in FIG. 17, "75,262,745" is input in the start position input field 62 and "75,262,810" is input in the end position input field 63 of the range of base coordinates to be displayed. Accordingly, in the display area 68, the range between 75,262,745 and 75,262,810 (base number 65) is indicated as the range of base coordinates, and thus the display range is further smaller than the range of base coordinates of FIG. 15 and FIG. 16.

In the display area 68 of FIG. 17, a reference sequence of chromosome A (the lowest part), base sequences of predetermined fragment data of chromosome samples X, Y, Z, and annotation data are displayed in a distinguishable mode. When the detailed view is displayed in this manner, the output data generator 207 in FIG. 3 may generate display data indicating a reference sequence, base sequences of fragmented data, and annotation data in a distinguishable mode. Also, when the large area is displayed as shown in FIG. 13 to FIG. 15, the output data generator 207 in FIG. 3 may generate display data indicating a reference sequence, base sequences of fragmented data, and annotation data in a distinguishable mode.

As described in the above with reference to FIG. 13 to FIG. 17, in accordance with the genome analysis device 2 according to the present embodiment, it is possible to easily enable seamless visualization from the histogram view of the overall image to the detailed base sequence view by using the mechanism of the Web browser.

FIG. 18 and FIG. 19 respectively show first and second specific examples of report data output by the genome analysis device according to the present embodiment.

The first specific example in FIG. 18 shows report data 400 concerning colon cancer. The report data 400 includes fields of gene name 401, chromosome locus 402, exon 403, mutation 404, dbSNP 405, mutation frequency of target gene in target disease 406, mutation frequency in target gene in mutated target disease 407, drug response 408, drug name 409, and source 410. Each information in each field is annotation data that is stored in correspondence with gene "KRAS" in the various information DB 214 (see FIG. 3).

In the first line of the report data 400, it is described that the locus (base position) in the chromosome of the gene "KRAS" indicated by gene name 401 is "12p12.1" (chromosome locus 402). It is also described that the frequency at which mutation indicated by mutation 404 occurs in the part of "exon 2" (exon 403) of the gene "KRAS" is "36-40%" (mutation frequency 406), and that the frequency of mutation in the target gene "KRAS" is "33.5-34.4%" (mutation frequency 407 in "KRAS" mutated colon cancer). The "rs112445441" described in dbSNP 405 indicates an identification number of information concerning mutation of the gene in dbSNP which is a database of SNP (Single Nucleotide Polymorphism). Since the second line of the report data 400 is the same as the first line, the description thereof will be omitted.

In the report data 400, it is also described that, regarding mutation of gene "KRAS" indicated by the first line and the second line, two kinds of drugs "cetuximab" and "panitumumab" indicated by drug name 409 are used, and these two kinds of drugs are not effective. In drug response 408, responsiveness of these two kinds of drug is described. It is also described that the source of such information concerning drug response is the document indicated by source 410.

Meanwhile, the second specific example in FIG. 19 shows report data 500 concerning breast cancer. The report data 500 includes fields of gene name 501, chromosome locus 502, exon 303, mutation 504, dbSNP 505, mutation frequency of target gene in target disease 506, mutation frequency in target gene in mutated target disease 507, drug response 508, drug name 509, and source 510. Each information in each field is annotation data that is stored in correspondence with gene "PIK3CA" in the various information DB 214 (see FIG. 3).

In the first line of the report data 500, it is described that the locus (base position) in the chromosome of the gene "PIK3CA" indicated by gene name 501 is "3q26.3" (chromosome locus 502). It is also described that the frequency at which mutation indicated by mutation 504 occurs in the part of "exon 9" (exon 503) of the gene "PIK3CA" is "26%" (mutation frequency 506), and that the frequency of mutation in the target gene "PIK3CA" in mutated colon cancer is "–11%" (mutation frequency 507). The "rs121913273" described in dbSNP 505 indicates an identification number of information concerning mutation of the gene in dbSNP which is a database of SNP. Since the second and the third lines of the report data 500 are the same as the first line, the description thereof will be omitted.

In the report data 500, it is also described that, regarding mutation of gene "PIK3CA" indicated by the first to the third lines, two kinds of drugs "trastuzumab" and "lap atinib" indicated by drug name 509 are used in combination, and these two kinds of drugs are not effective. In drug response 508, responsiveness of these two kinds of drug is described. It is also described that the source of such information concerning drug response is the website on the Internet indicated by the source 510.

The report data 400 and the report data 500 that have been described with reference to FIG. 18 and FIG. 19 are generated by the processing according to subsequent steps S22 to S24 when the output request 13 is a request concerning output of the report data in the processing according to step S21 in FIG. 12.

That is, in step S23, the output data generator 207 (plurality of the worker instances 271) selects and reads out data from the storage 209 (S23). Here, annotation data that is brought into correspondence with gene (for example, "KRAS" or "PIK3CA") is selected and read out. Subsequently, the flow proceeds to step S24 where report data such as report data 400, 500 is generated based on the selected and read out data (S24).

In particular, when mutation of gene corresponding to a predetermined disease is detected as a result of the analysis by the genome analysis device 2, the output data generator 207 may generate the report data 400, 500 as shown in FIG. 18 and FIG. 19. Thus, an operator of the client device 3, for example, a physician can use the generated report data for medical diagnosis of a predetermined disease (for example, "colon cancer" or "breast cancer" described above).

Annotation data for each gene stored in the various information DB 214 is not limited to the data illustrated in FIG. 18 and FIG. 19. For example, it may be data indicating past diagnosis information concerning the gene, basic experiment information, patent literature information closely related with drugs, or the like.

While one embodiment of the present invention has been described above, the above embodiment merely indicates one of application examples of the present invention, and is not intended to limit the technical scope of the present invention to specific configuration of the above embodiment.

REFERENCE SIGNS LIST

1: Genome analysis system
2: Genome analysis device
3: Client device
4: Network
11: Genome data
12: Analysis request
13: Output request
14: Response
201: Data receiver
202: Request issuer
203: Request receiver
204: Task controller
205: Preprocessor
206: Analyzer
207: Output data generator
208: Data transmitter
209: Storage
211: File DB
212: Sequence DB
213: Coverage DB
214: Various information DB
215: Cache

The invention claimed is:

1. A genome analysis device configured to analyze genome data including 3,000 or more fragmented genome base sequences output from a sequencer and transmit output data concerning the genome data in response to an output request from a client device connected via a network, the genome analysis device comprising:
 a non-transitory storage unit comprising a stored program and configured to store data, and
 a processing unit connected to the storage unit,
 wherein the program is configured to cause the processing unit to:
  calculate, for different bin sizes and different ranges of base coordinates, coverages between the genome data and a reference sequence of the chromosome corresponding to the genome data;
  store the calculated coverages in the storage unit;
  receive an output request from the client device;
  select a coverage for a bin size and a range of base coordinates which correspond to the output request from the coverages stored in the storage unit when the processing unit receives the output request; and
  generate output data based on the selected coverage.

2. The genome analysis device according to claim 1, wherein when the processing unit receives the output request, the processing unit generates display data for displaying the selected coverage by a histogram.

3. The genome analysis device according to claim 1, wherein the processing unit further brings annotation data into correspondence with each of different ranges of base coordinates and stores the annotation data in the storage unit.

4. The genome analysis device according to claim 3, wherein when the processing unit receives the output request, the processing unit selects annotation data in a range of base coordinates designated by the output request from the storage unit, and generates display data for displaying the selected annotation data.

5. The genome analysis device according to claim 1, wherein the display data has a data range that is broader than a range to be displayed in a display area of the client device.

6. A genome visualization method for analyzing genome data by a genome analysis device, the genome data including 3,000 or more fragmented genome base sequences output from a sequencer, and for transmitting output data concerning the genome data in response to an output request from a client device connected via a network, the genome analysis device comprising a processing unit and a non-transitory storage unit,
 the genome visualization method comprising:
  calculating, for different bin sizes and different ranges of base coordinates, coverages between the genome data and a reference sequence of the chromosome corresponding to the genome data;
  storing the calculated coverage in the storage unit;
  receiving an output request from the client device;
  selecting a coverage for a bin size and range of base coordinates which correspond to the output request from the coverages stored in the storage unit when the processing unit receives the output request; and
  generating output data based on the selected coverage.

7. The genome visualization method according to claim 6, wherein the display data has a data range that is broader than a range to be displayed in a display area of the client device.

* * * * *

SEQUENCE LISTING

```
<160> NUMBER OF SEQ ID NOS: 1

<210> SEQ ID NO 1
<211> LENGTH: 61
<212> TYPE: DNA
<213> ORGANISM: Homo sapiens

<400> SEQUENCE: 1
aaggccgacg cggaggttaa gctcattctg taccattgga cgcattcgtt cagctctcaa      60
a                                                                      61
```